United States Patent [19]

Warren et al.

[11] Patent Number: 5,200,045
[45] Date of Patent: Apr. 6, 1993

[54] AGAROSE PLATE PRESS

[75] Inventors: Barbara M. Warren, Beaumont; James R. M. Sanford, Vidor; Edgar F. Neely, Kountze; Robert J. Sarrine, Beaumont, all of Tex.

[73] Assignee: Helena Laboratories Corporation, Beaumont, Tex.

[21] Appl. No.: 902,000

[22] Filed: Jun. 22, 1992

Related U.S. Application Data

[62] Division of Ser. No. 523,709, May 1, 1990.

[51] Int. Cl.$^5$ .................. G01N 27/26; G01N 27/447; G01N 33/561; G01N 33/537
[52] U.S. Cl. ............................ 204/180.1; 204/299 R; 204/182.8; 436/516; 436/538; 436/539
[58] Field of Search ............ 204/299 R, 182.8, 180.1; 436/516, 538, 539

[56] References Cited

U.S. PATENT DOCUMENTS 4,716,101 12/1987 Thompson et al. ............ 436/516 X
5,149,408 9/1992 Perlman ...................... 204/180.1 X

FOREIGN PATENT DOCUMENTS 8504256 9/1985 PCT Int'l Appl. .............. 204/180.1

OTHER PUBLICATIONS

Claus Koch, Karsten Skjodt, and Inga Laursen, "A Simple Immunoblotting Method after Separation of Proteins in Agarose Gel" Journal of Immunological Methods 84 (1985) 271-278.

Primary Examiner—John Niebling
Assistant Examiner—John S. Starsiak, Jr.
Attorney, Agent, or Firm—Spencer, Frank & Schneider

[57] ABSTRACT

A method and apparatus for removing unreacted protein and unreacted antisera from a gel plate during immunofixation electrophoresis. The apparatus includes a pressure plate movable toward and away from a fixed base for exerting a desired force on the electrophoresis plate. A stop member limits the movement of the pressure plate toward the fixed base thus controlling the amount of pressure on the electrophoresis plate.

1 Claim, 2 Drawing Sheets

AGAROSE PLATE PRESS

This is a division of application Ser. No. 07/523,709 filed May 1, 1990.

BACKGROUND OF THE INVENTION

The present invention relates to immunofixation electrophoresis procedures in general and, more specifically, to improved method and apparatus for removal of unprecipitated chemicals as an intermediate step in the immunofixation electrophoresis process.

DESCRIPTION OF THE PRIOR ART

Immunofixation electrophoresis (IFE) is a two-stage procedure utilizing agarose gel protein electrophoresis in the first stage and immunoprecipitation in the second stage. The specimen or sample is typically serum, urine, or cerebral spinal fluid. There are numerous applications for IFE in research, forensic medicine, genetic studies and clinical laboratory procedures and the greatest demand of IFE is in the clinical laboratory where it is primarily used for the detection and identification of monoclonal immunoglobin gammopathies.

Prior to the present invention, Helena Laboratories Corporation of Beaumont, Tex., assignee of the present invention, marketed materials for IFE. Following the recommended procedure, the patient sample would be electrophoresed to obtain protein resolution or separation. That concluded the electrophoresis stage of the procedure. Thereafter, in the second stage, a soluble antigen and its antibody are allowed to react. The resultant antigen-antibody complexes may become insoluble as long as the amount of antibody is in slight excess or near equivalency, and the complexes will precipitate. The precipitation rate depends upon the proportions of the reactants, temperature, salt concentration, and the pH of the solution. The unreacted proteins and the unreacted antisera are removed by repetitive washing and drying steps and thereafter the antigen-antibody complexes (which might be visible as a white cloudy band in unstained gel against a dark background) is then visualized by staining.

Prior to the present invention, the procedure for removing unreacted proteins, as recommended by Helena Laboratories Corporation, assignee of the present invention, included 10 minute washing of the gel in a saline solution, and then heavy pressure (such as from a block of metal on the gel to remove unprecipitated and unreacted proteins and reagents). The wash cycle was about 10 minutes and the pressure under a heavy weight (a 2¼ lb. weight was recommended by Helena) was also recommended to be carried out for 10 minutes. Then the washing and pressing steps were repeated and thus a complete washing and pressing cycle encompassed 40 minutes. Of course multiple agarose shell plates could be placed in a vertical stack and subjected to the pressure simultaneously.

SUMMARY OF THE INVENTION

The present invention provides a new approach to the procedure of removing unreacted proteins and unreacted antisera through the use of a novel press which essentially reduces the washing/pressing cycle from 40 minutes to about 10 minutes.

The agarose plate press of the present invention includes a generally flat, fixed base and a generally flat pressure plate mounted for movement toward and away from the base. The distance between the base and the pressure plate is adjustable and is initially established based on the number of agarose gel plates which are being processed. A mounting system for the pressure plate allows the pressure plate to be moved into contact with the agarose plate (or vertical stack or agarose plates). The press of the present invention includes biasing means to exert a desired force on the agarose plate (or stack of agarose plates) and the press includes an indicator to confirm that the correct amount of pressure is being placed on the plates.

BRIEF DESCRIPTION OF THE DRAWINGS

The various objects, benefits and advantages of the present invention will become more apparent upon reading the following detailed description of the invention taken in conjunction with the drawings. In the drawings, wherein like reference numerals identify corresponding components.

DETAILED DESCRIPTION OF THE INVENTION

With reference to the drawings, a press 10 is illustrated which is to be used in removing unreacted proteins from one or more agarose gel plates 12. The gel plates 12 are shown, solely for illustrative purposes, as being of generally rectangular configuration and arranged as a plurality of plates in a vertical stack 14.

Figure 1:
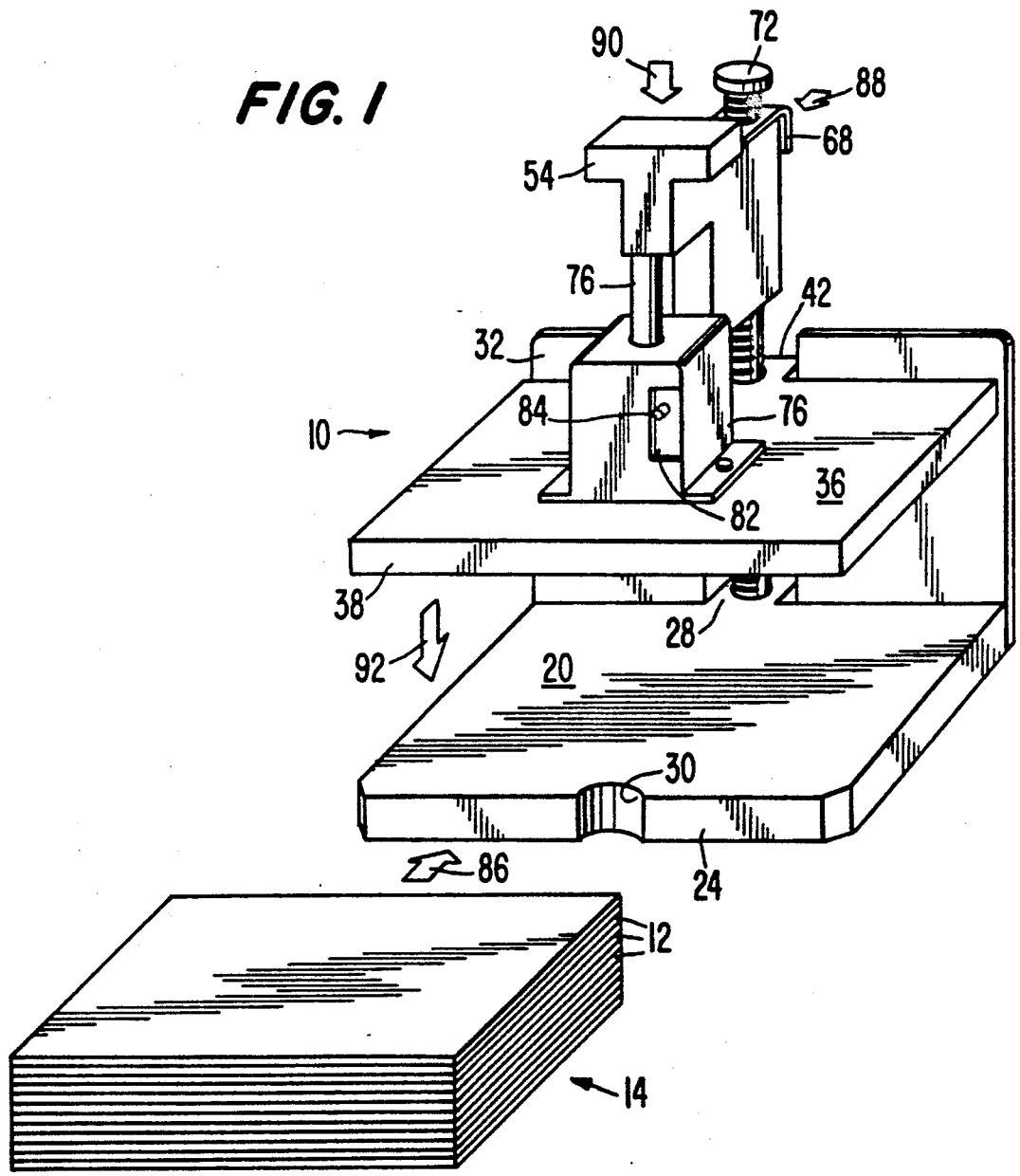
FIG. 1 is a perspective illustration of the press of the present invention and diagrammatically illustrating a vertical stack of agarose plates to be inserted into the press.
Figure 2:
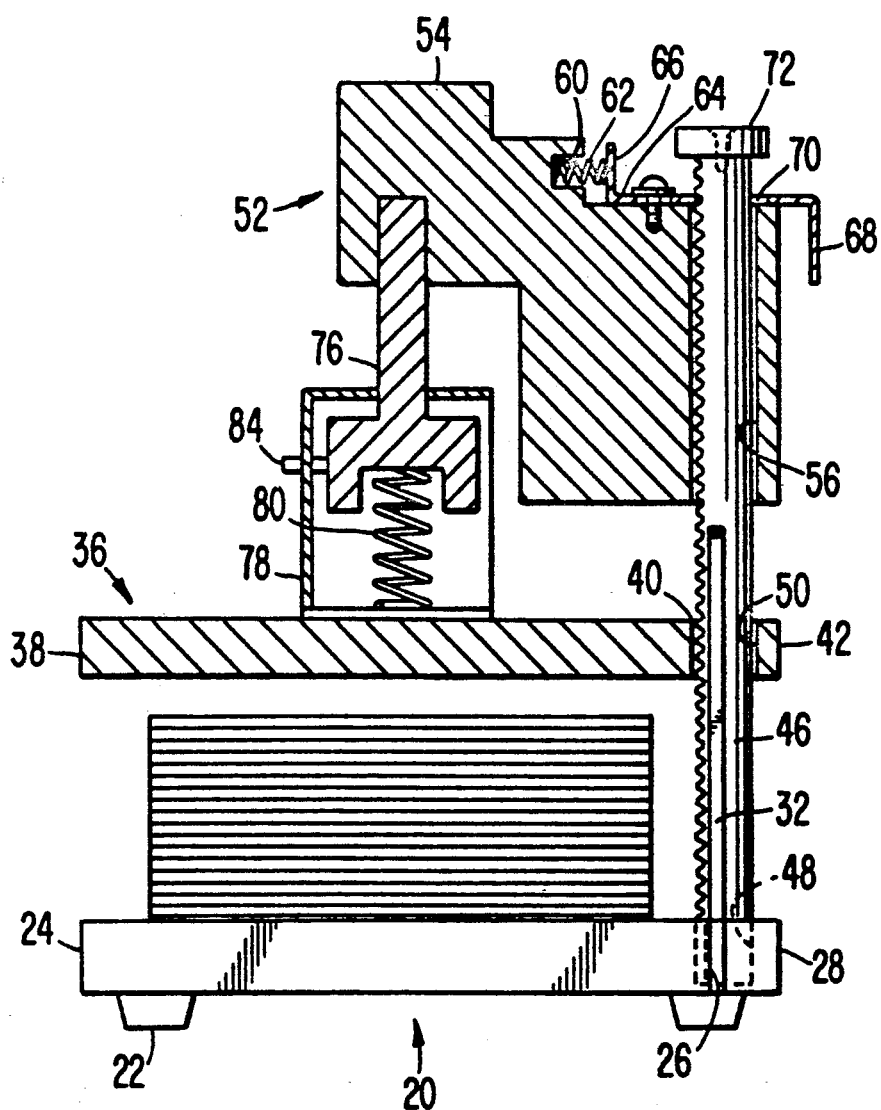
FIG. 2 is a side view, partly in section, illustrating the press of the present invention with a stack of agarose plates in position within the press.

The press has a generally flat rectangular base 20 with an upper bearing surface and downwardly depending support feet 22 which are not illustrated in FIG. 1. The base 20 includes a front 24 and a rear 26 and opposed sides. A rearwardly extending projection 28 is positioned intermediate the sides of the base 20. The front surface 24 of the base may include a recess 30 to facilitate removal of the gel plates. The front corners of the base are illustrated as chamfered. Extending upwardly from the generally horizontal base 20 are a pair of backstops 32 each which may be secured to the rear 26 of the base by conventional screw fasteners. The two backstops 32 are on opposite sides of the rear projection 28. When one or more agarose gel plates 12 are placed on the horizontal base 20, the vertically positioned backstops limit the degree of insertion of the plates into the press.

The press of the present invention includes a platen or pressure plate 36 which is also generally rectangular in configuration in the illustrated embodiment and is mounted above the base 20 for vertical movement toward and away from the base. It is important, for optimum results, that the pressure plate be at least the same size and shape as the agarose gel plates. The pressure plate 36 is illustrated as having a front 38 and a rear 40 and opposed ends. A projection 42 extends rearwardly from the rear of the pressure plate 36 intermediate the ends. The projection 42 should be positioned and aligned above the projection 28. The rear 40 of the pressure plate is positioned forwardly of the backstops 32. Thus the projection 28 on the base and the projection 42 on the pressure plate both extend rearwardly of the backstops 32.

Means are provided for mounting the pressure plate for movement toward and away from the base such that force may be applied to agarose gel plates positioned between the pressure plate 36 and the base 20. The mounting means includes a toothed rack 46 which may be of generally circular cross section. The toothed rack is positioned vertically with a lower end in a suitable aperture 48 in the rear projection 28. The toothed rack extends through a suitable aperture 50 in the rear projection 42.

The mounting means also includes a slide block 52. Slide block 52 includes a handle or other suitable gripping means 54 at its top forward portion. A vertical bore 56 extends through the block and the toothed rack is positioned within the vertical bore. The slide block moves vertically along the toothed rack.

A rearwardly opening recess 60 is provided in the slide block 52 and a spring 62 is positioned in the recess. A latch 64 is provided for selectively engaging teeth of the toothed rack 46 for thus vertically positioning the slide block 52. the latch 64 is a thin, generally horizontal, flat member having a upwardly extending front portion 66 and downwardly extending rear portion 68. The upwardly extending front portion of the latch is secured to one end of the spring 62. A fastener is provided through a suitable slot to maintain the generally horizontal portion of the latch in contact with the slide block. A slot 70 is formed in the generally horizontal portion of the latch and the edge of the slot is of suitable thickness to engage teeth of the toothed rack 46. The spring 62 urges the slot 70 rearwardly to engage the toothed rack 46. Forward pressure on the rear portion 68 or the latch compresses spring 62 and disengages the edge of the slot 70 from the rack such that the slide block may be moved vertically.

To assemble the press, the rack 46 may conveniently be inserted through the apertures 50 and 48 in the rear projections of the pressure plate and base. Thereafter, the slide block may be lowered into position such that the rack enters the bottom of the bore 56, and as the slide block is moved downwardly, the rack will move along the bore 56 and emerge from the top of the bore. A cap or rack stop 72 may then be fastened to the top of the toothed rack. This prevents accidental disassembly of the press and limits vertical upward movement of the slide block. The length of the slot 70 is such that even upon engagement of the slot edge with a tooth in the rack, spring 62 is still partially compressed and thus will not fall free of the recess 60.

Means are provided for exerting pressure or force on the agarose gel plates. A piston assembly 76 has one end fixed within the slide block and extends vertically downwardly toward the pressure plate. The piston assembly extends into a housing 78 which is mounted such as by screw fasteners to the upper surface of the pressure plate 36. A spring 80 is positioned within the housing and one end of the spring engages upper surface of the pressure plate 36 while the other end of the spring engages the piston 76 assembly interiorly of the housing.

Means are provided for controlling the amount of force applied to the agarose gel plates. In this regard, the housing includes an elongated vertical window or slot 82. A stop member 84, illustrated in the drawings as a small elongated cylinder, has one end secured to the piston assembly interiorly of the housing 78, and the stop member or cylinder extends outwardly of the housing through the window or slot 82.

The operation of the press of the present invention will now be explained and it should be appreciated that the operation is the same whether one agarose gel plate or a vertical stack of agarose gel plates are to be positioned in the press.

The agarose plate or plates are positioned on the press between the base 20 and the pressure plate 36 such as by inserting the plates in the direction of arrow 86 in FIG. 1. Backstop 32, of course, limits the degree of insertion of the agarose plates. The latch 64 and specifically the rear portion 68 is moved forwardly such as in the direction of arrow 88 to disengage the latch from the toothed rack. The pressure plate 36 will move downwardly as illustrated by arrows 90 and 92 and this downward movement may be guided by gripping the slide block handle 54. Manual downward pressure on the slide block 54 should continue until the stop member 84 engages the lower edge of the window or slot 82. This provides the desired, controlled amount of force on the agarose gel plates. In the preferred embodiment, the press is fabricated of metal, except for the protective feet 22 and the spring may be a 15 pound compression spring.

According the principles of the present invention, when the press is used to remove unreacted proteins and unreacted antisera from agarose gel plates during the IFE procedure, absorbent blotters are placed between agarose plates as is conventional. As compared to the previously described process of twenty minutes for each wash-press cycle with two complete cycles preferred thus totalling 40 minutes, the present invention requires an initial wash step of merely quickly immersing the plates in saline solution, a first press cycle of about 5 minutes, a four minute wash cycle and second press cycle of about 1 minute. Thus the present invention has reduced a forty minute procedure to about a 10 minute procedure.

According to the present invention the movable platen or pressure plate 36 is about $3\frac{3}{4} \times 6\frac{1}{4}$ inches. When larger agarose plates are used (typically $3\frac{1}{4} \times 5\frac{1}{2}$ inches), the actual pressure is about 0.84 psi. When small agarose plates are used (typically $3\frac{1}{4} \times 3\frac{3}{4}$ inches), the actual pressure is about 1.23 psi.

The foregoing is a complete description of a preferred embodiment of the present invention. Numerous changes may be made without departing from the spirit and scope of the present invention. The invention, therefore, should be limited only by the following claims.

What is claimed is:

1. In a method of immunoelectrophoresis wherein protein separation is performed in an electrophoresis gel and thereafter at least one antiserum is applied to the separated proteins for immunoprecipitation, the method further including removing unreacted protein and unreacted antisera from the electrophoresis plate, the improvement comprising:

positioning at least one electrophoresis plate in a press of a type having a fixed base and a moveable pressure plate, the electrophoresis gel plate being positioned between the fixed base and the moveable pressure plate;

moving the pressure plate toward the fixed base to exert pressure on the electrophoresis gel; and limiting the degree of movement of the pressure plate toward the fixed base to control the amount of pressure on the electrophoresis gel plate.

* * * * *